United States Patent [19]

Alexander et al.

[11] Patent Number: 5,079,361
[45] Date of Patent: Jan. 7, 1992

[54] THIOL-REACTIVE CROSS-LINKING REAGENTS

[75] Inventors: Rikki P. Alexander, High Wycombe; Michael A. W. Eaton, Aston Rowant; Thomas A. Millican; Richard C. D. Titmas, both of Maidenhead, all of United Kingdom

[73] Assignee: Celltech Limited, Slough, United Kingdom

[21] Appl. No.: 246,548

[22] PCT Filed: Jan. 15, 1988

[86] PCT No.: PCT/GB88/00028
§ 371 Date: Sep. 9, 1988
§ 102(e) Date: Sep. 9, 1988

[87] PCT Pub. No.: WO88/05433
PCT Pub. Date: Jul. 28, 1988

[30] Foreign Application Priority Data

Jan. 15, 1987 [GB] United Kingdom ............ 8700859
Aug. 12, 1987 [GB] United Kingdom ............ 8719040

[51] Int. Cl.$^5$ ............ C07D 251/12; C07D 251/22; C07D 239/24; C07D 239/28; C07D 213/62; C07D 211/72; C07D 211/84

[52] U.S. Cl. ............ 544/216; 544/180; 544/194; 544/196; 544/197; 544/198; 544/199; 544/204; 544/208; 544/209; 544/210; 544/211; 544/212; 544/213; 544/215; 544/219; 544/330; 544/332; 544/335; 544/242; 544/297; 544/298; 544/315; 544/316; 544/317; 544/318; 544/319; 544/320; 544/321; 546/261; 546/262; 546/256; 546/263; 546/264; 546/265; 546/266; 546/267; 546/329; 546/330; 546/331; 546/334; 546/335; 546/336; 546/255; 546/281; 546/286; 546/287; 546/288; 546/289; 546/290; 546/291; 546/292; 546/293; 546/296; 546/297; 546/298; 546/299; 546/300; 546/301; 546/302; 546/303; 546/304; 546/305; 546/310; 546/312; 546/338; 546/339; 546/340; 546/341; 546/342; 546/346

[58] Field of Search ............ 544/330, 332, 335, 242, 544/297, 298, 315, 316, 317, 318, 319, 320, 321, 180, 194, 196, 197, 198, 199, 204, 208, 209, 210, 211, 212, 213, 215, 216, 219; 546/261, 262, 256, 263, 264, 265, 266, 267, 329, 330, 331, 334, 335, 336, 255, 281, 286, 287, 288, 289, 290, 291, 292, 293, 296, 297, 298, 299, 300, 301, 302, 303, 304, 305, 310, 312, 337, 338, 339, 340, 341, 342, 346

[56] References Cited

U.S. PATENT DOCUMENTS 3,872,152 3/1975 Lehr .................... 544/194

FOREIGN PATENT DOCUMENTS 0175617 3/1986 European Pat. Off. ............ 544/330

Primary Examiner—Johann Richter
Attorney, Agent, or Firm—Nixon & Vanderhye

[57] ABSTRACT

Cross-linking reagents which are highly specific for sulphydryl groups and react with thiols at an excellent rate. The essential feature of the reagents is at least one vinyl group conjugated with an aromatic nitrogen heterocycle. Particular examples include vinyl pyridines, vinyl pyrimidines and vinyl triazines.

6 Claims, No Drawings

THIOL-REACTIVE CROSS-LINKING REAGENTS

FIELD OF THE INVENTION

This invention relates to cross-linking reagents, each comprising at least one thiol-reactive functional group covalently linked to at least one other reactive functional group, and to processes for their preparation. More particularly the invention relates to heterofunctional cross-linking reagents, each comprising at least one thiol-reactive functional group covalently linked to at least one, different, reactive functional group, and to processes for their preparation.

BACKGROUND TO THE INVENTION

Cross-linking reagents are well known and a considerable range of such reagents is available commercially. In broad terms, a cross-linking reagent comprises two or more reactive functional groups covalently linked together. The covalent linkage may be direct, but in many cases the reactive functional groups are spaced apart by respective covalent attachment to a spacer linkage. The reactive functional groups may be the same or may be different, (a heterofunctional cross-linking agent).

One application of cross-linking reagents is in the production of conjugate compounds which comprise a polypeptide or protein covalently attached to another chemical entity. Examples of such conjugate compounds include: antibody covalently attached to a signal producing chemical entity such as an enzyme or a chelated radioopaque or radioactive metal atom; antibody covalently attached to a cytotoxic chemical entity such as a toxin or a chelated radioactive metal atom; and an enzyme covalently attached to an antigenic analyte.

There is considerable interest in the use of cross-linking reagents for linking antibody or antibody fragments to signal-producing chemical entities or to cytotoxic chemical entities for use in diagnosis and cell-targeted therapy. It is known to produce such conjugate molecules using heterofunctional reagents which have a thiol-reactive functional group covalently linked to a different functional group such as an amino-reactive activated ester. Thus the heterofunctional cross-linking reagent is first reacted with the chemical entity to which it is desired to attach antibody. This may be done, for example, by reacting amino groups on the chemical entity with the amino reactive functional group on the heterofunctional cross-linking reagent. Next, free sulphydryl groups on the antibody or antibody fragment are reacted with the thiol-reactive functional group on the heterofunctional cross-linking reagent to yield the desired conjugate molecule.

Heterobifunctional cross-linking reagents (that is, heterofunctional cross-linking reagents with two reactive functional groups) are known which employ maleimides as the thiol-sepcific functional groups. An example of such a reagent is n-maleimido-benzoyl-N-hydroxysuccinimide ester (MBS) which has been used to prepare conjugate molecules comprising antibody or antibody fragments and enzymes or cytotoxic compounds. (O'Sullivan, M. J. et al, (1979), Anal. Biochem., 100, 100–108; Freytag, J. W. et al, (1984), Clin. Chem., 30, 417–420; Youle, R. J. et al, (1984), PNAS USA, 77, 5483–5486). Various derivatives of maleimide-based heterobifunctional cross-linking reagents are also known. The maleimide reagents are very reactive and readily hydrolyse to maleamic acid. They are, in general, of low specificity for sulphydryl groups, particularly when used at the pH and in the stoichiometric amounts that are often necessary for the preparation of conjugate molecules, to ensure that the resulting molecule has only one of each conjugated group.

Heterobifunctional cross-linking reagents are also known which employ $\alpha$-halo acid derivatives as the thiol specific functional group. Whilst less reactive than the maleimide reagents, they are readily hydrolysed to the corresponding $\alpha$-hydroxy acid derivatives and their tautomers. The aldehyde tautomers are essentially non-specific and reduce the overall specificity of the $\alpha$-halo acid derivatives for thiol groups.

The low specificity of the known heterobifunctional cross-linking reagents can result in the production of complex mixtures of reaction products. The complex mixtures arise from non-specific reaction of the thiol reacting group with non-thiol groups of the antibody or the linked chemical entity. For example, the known thiol reacting groups commonly exhibit competitive reactivity for amine groups which can lead to complex polymerisation products. Unwanted side reactions are particularly disadvantageous where the linked chemical entity possesses secondary amines such as saturated ring nitrogens (e.g. in macrocyclic chelating ligands). Not only are these mixtures difficult to separate, but where the conjugate compound is for in vivo use, absolute purity is of paramount importance.

In the unconnected field of protein identification using HPLC it has been noted that 4-vinyl pyridine can be used as a specific marker for cysteine residues (Fullmer, C. S. et al, (1984), Anal. Biochem. 142, 336–339).

SUMMARY OF THE INVENTION

According to the present invention, there is provided a cross-linking reagent comprising at least one thiol-reactive functional group covalently linked to at least one other reactive functional group, characterised in that the thiol-reactive functional group comprises a vinyl group conjugated with an aromatic nitrogen heterocycle, or a derivative thereof.

In a preferred aspect of the invention we provide a heterofunctional cross-linking reagent comprising at least one thiol-reactive functional group covalently linked to at least one different reactive functional group, characterised in that the thiol-reactive functional group comprises a vinyl group conjugated with an aromatic nitrogen heterocycle, or a derivative thereof.

In the compounds according to the invention, the aromatic nitrogen heterocycle may have one, two or three nitrogen atoms, the vinyl group being o or p to at least one of the nitrogen atoms in each case. One or two vinyl groups may be provided on each aromatic nitrogen heterocycle. The vinyl group may be geminally substituted with two aromatic nitrogen heterocycles. The nitrogen heterocycle(s) and/or the vinyl group(s) may each be substituted by an electron withdrawing group. The other functional group may be covalently attached, optionally via a spacer linkage, either directly to the aromatic nitrogen nucleus, or geminally with the aromatic nucleus to the vinyl group. Preferably the thiol-reactive functional group is a derivative of 2-vinyl pyridine.

It will be apparent that the present invention relates particularly to the thiol-reactive functional group of the cross-linking reagent. The remainder of the reagent may be of conventional type. The other functional group (or groups) may be any group capable of forming a covalent bond with a further chemical entity. In the preferred compounds, the functional group is an activated ester. Similarly, the two functional groups may be covalently linked via a spacer linkage. The linkage may be selected to provide optimum spacing between the functional groups and may be selected to provide desired properties of solubility and flexibility of the linkage. The essential feature of the thiol-reactive functional group is a vinyl group, conjugated with an aromatic nitrogen heterocycle.

We have discovered that heterofunctional cross-linking reagents of the present invention have a markedly improved specificity for sulphydryl groups compared with the reagents of the prior art. The improvement is particularly marked where one or both of the compounds to be linked possesses secondary amines, particularly saturated ring nitrogens. Certain compounds of the invention, especially compounds of formulae (2), (3) and (4) described below, also advantageously react with thiols at an excellent rate.

Particular examples of heterrobifunctional cross-linking reagents according to the invention are compounds of formulae (1a)–(1m):

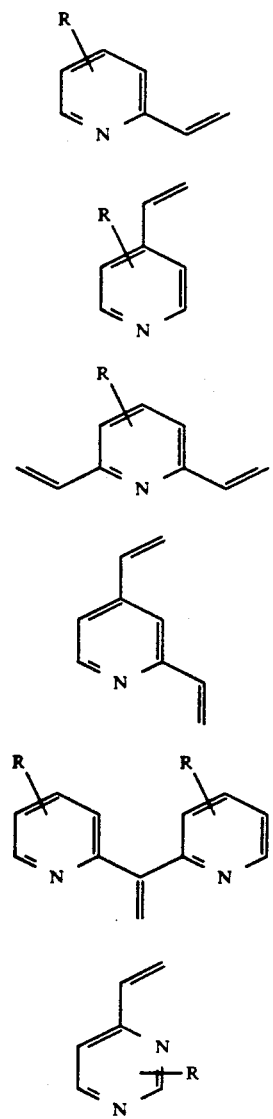

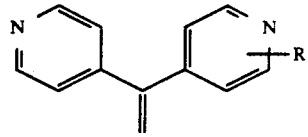

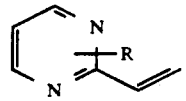

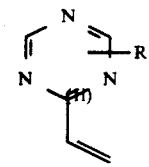

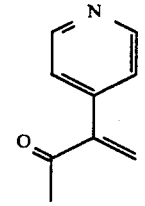

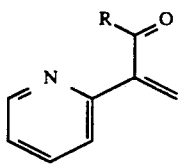

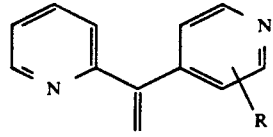

or

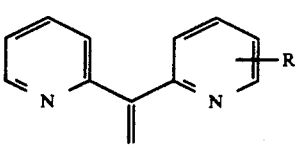

and derivatives thereof wherein at least one nitrogen heterocycle and/or vinyl group is substituted by an electron withdrawing group, where R is the other functional group, optionally linked via a spacer linkage.

In the compounds of formulae (1a)–(1m) R is preferably an activated ester.

Particularly useful cross-linking reagents are the compounds of formulae (1a) and (1m) and derivatives thereof wherein at least one nitrogen heterocycle and/or vinyl group is substituted by an electron withdrawing group.

A particularly preferred group of compounds among these types has the formula (2):

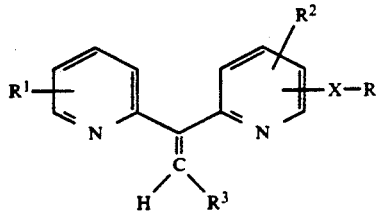

(2)

wherein X is a covalent bond or a spacer group; R is a functional group; and $R^1$, $R^2$ and $R^3$, which may be the same or different, is each a hydrogen atom or an electron withdrawing group.

In the compounds of formula (2), the functional group R may be for example an activated ester, for example a group —$CO_2R^4$ where $R^4$ is an aryl group such as a substituted phenyl group e.g. a nitrophenyl group such as a p-nitrophenyl group, or an imide group such as

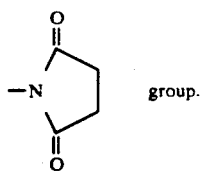 group.

When X is a spacer group it may be for example $C_{1-6}$alkylene (e.g. ethylene, propylene), optionally substituted by phenylene, $C_{1-3}$alkoxy$C_{1-3}$alkylene (e.g. methoxymethylene, methoxyethylene), phenylene, or $C_{5-7}$cycloalkyl$C_{1-3}$alkylene (e.g. cyclohexylmethylene).

When $R^1$, $R^2$ or $R^3$ is an electron withdrawing group it may be for example a halogen atom or a —$NO_2$, —$CO_2H$, —$CO_2R^5$ (where $R^5$ is a $C_{1-4}$alkyl group) —$COR^5$, —CHO, —CN, —$CF_3$, —$SO_2NR^5R^6$ (where $R^6$ is as defined for $R^5$) or a phenyl group.

When $R^1$, $R^2$, or $R^3$ is a halogen atom it may be a fluorine, chlorine, bromine or iodine atom.

A particularly useful group of compounds of formula (2) has the formula (3):

(3)

(wherein X and R are as defined previously).

Compounds of this type in which R is a group —$CO_2R^4$ where $R^4$ is as defined previously are preferred.

Particularly preferred compounds according to the invention have the formula (4):

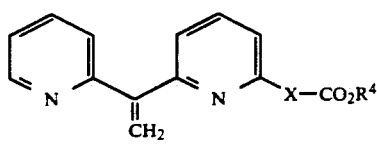

(4)

where X is a $C_{1-3}$alkoxy$C_{1-3}$alkylene, especially methoxymethylene group and $R^4$ is a nitrophenyl, particularly p-nitrophenyl,

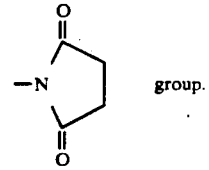 group.

The compounds according to the invention may be prepared by the processes described below. Thus in general compounds of formulae (1a)–(1m) may be prepared from known pyridyl, bipyridyl, pyrimidinyl or triazinyl starting materials by reactions designed to allow the introduction of one or more vinyl groups. Such syntheses are described below specifically for the preparation of compounds of formula (1j), (1k) and (1m), but are equally applicable to the preparation of other compounds of formula (1).

Thus, compounds of formula (1m) in which R is a group —X—$CO_2R^4$ may be prepared by esterification of salts of formula (5):

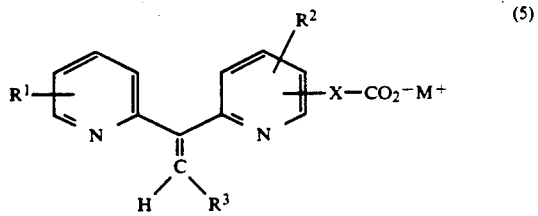

(5)

(where $M^+$ is a cation, for example a metal ion such as a sodium ion, or a pyridinium ion) or reactive derivatives thereof (e.g. anhydrides) using an alcohol $R^4OH$ optionally in the presence of a coupling agent such as dicyclohexyl carbodiimide. The reaction may be performed in an appropriate solvent, for example a halogenated hydrocarbon such as dichloromethane at any suitable temperature, e.g. ambient temperature.

The salts of formula (5) may be prepared by hydrolysis of a corresponding alkyl ester of formula (6):

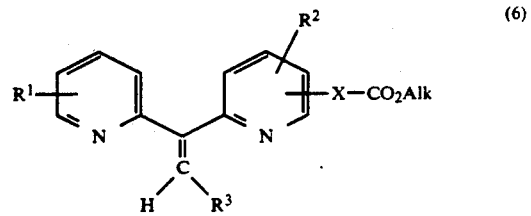

(6)

(where Alk is for example an alkyl group such as a methyl group) using for example a base, e.g. an inorganic base such as sodium hydroxide or lithium hydroxide in a solvent such as dichloromethane followed where necessary by cation exchange, using conventional procedures, to substitute any desired cation.

Intermediates of formula (6) may be prepared using a corresponding ketone of formula (7):

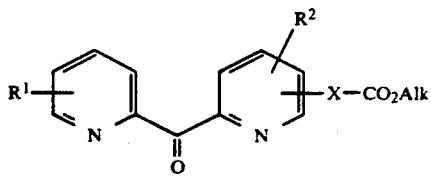

(7)

and a reagent $(R^7)_3P=CHR^3$ (where $R^7$ is for example an aryl group such as a phenyl group) in a solvent such as an ether, e.g. a cyclic ether such as tetrahydrofuran, at a low temperature e.g. $-10°$ to $-100°$ C., such as $-78°$ C. or a reagent $(CH_3)_3SiCHR^3MgCl$ in the presence of thionyl chloride in a solvent such as tetrahydrofuran at a temperature such as $0°$ C.

The reagents $(R^3)_3P=CH_2$ and $(CH_3)_3SiCHR_3MgCl$ may be prepared using standard procedures.

The intermediate ketones of formula (7) may be prepared by oxidation of a corresponding alcohol of formula (8):

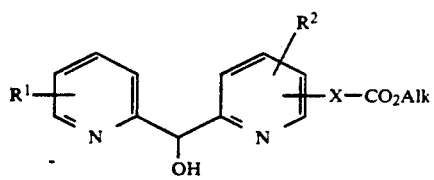

(8)

using an oxidising agent, such as manganese dioxide in a solvent such as dichloromethane, at, for example, room temperature.

In general, the alcohols of formula (8) may be prepared by reaction of an appropriate 2-lithiopyridine (prepared by standard procedures from the corresponding 2-halopyridine) with an aldehyde of formula (9):

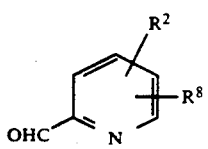

(9)

(where $R^8$ is the group $-X-CO_2Alk$ or a precursor thereof) in the presence of n-butyl lithium, at a low temperature e.g. $-78°$ C. in a solvent such as tetrahydrofuran, followed where necessary by conversion of any group $R^8$ to the group $-X-CO_2Alk$.

The aldehyde of formula (9) may be prepared by oxidation of the corresponding pyridine methanol using for example manganese dioxide in a solvent such as dichloromethane at e.g. room temperature. The pyridine methanol starting materials for this reaction are either known compounds or may be prepared by methods analogous to those used for the preparation of the known compounds.

In a particular example of this general reaction scheme, a compound of formula (8) in which X is an alkoxyalkylene group may be prepared in several steps, firstly by reacting a compound of formula (9) in which $R^8$ is a group $-(CH_2)_mOR^9$, (where m is an integer 1 to 3 and $R^9$ is a protecting group such as a dimethoxytrityl group), with a 2-lithiopyridine as described above to yield a compound of formula (8) in which the group $-X-CO_2Alk$ is replaced by $-(CH_2)_mOR^9$. Protection of the alcohol function of this intermediate using standard procedures and a different protecting group to $R^9$, for example by silylation using a silyl halide and a base such as imidazole in a solvent such as dimethylformamide, yields the bis-protected compound (10):

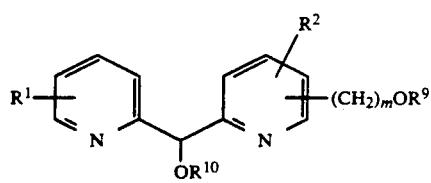

(10)

(where $R^{10}$ is a protecting group different to $R^9$ for example a t-butyldiphenylsilyl group), which may then be selectively deprotected to yield the alcohol (11):

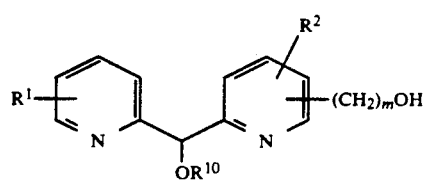

(11)

for example using anhydrous zinc bromide in dichloromethane when the group $R^9$ is dimethoxytrityl and $R^{10}$ is t-butyldiphenylsilyl. The alcohol (11) may then be alkylated, using for example an appropriate haloalkanoate, n-butyl lithium, a solvent such as tetrahydrofuran and a low temperature e.g. $-78°$ C., with subsequent removal of the protecting group $R^{10}$ using conventional procedures (for example silyl groups may be removed using tetrabutylammonium fluoride in a solvent such as tetrahydrofuran) to yield the desired intermediate of formula (8).

Compounds of formula (9) in which $R^8$ is a group $-(CH_2)_mOR^9$ may be prepared by protection of the corresponding alcohol (i.e. where $R^9$ is $-OH$) using conventional protection procedures. The alcohol starting materials for this reaction are either known compounds or may be prepared by methods analogous to those used for the preparation of the known compounds.

The intermediate compounds of formulae (5), (6), (7), (8), (9) (10) and (11) are novel compounds and form further aspects of the invention.

In a further process, compounds of formulae (1j) and (1k) may be prepared using as starting materials pyridines of formulae 12(a) or 12(b):

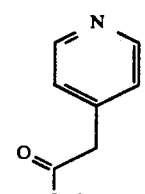

12(a)

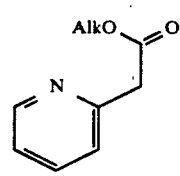

12(b)

Reaction of these compounds with lithium diisopropylamide followed by a phenylselenenyl halide, e.g. chloride, in a solvent such as tetrahydrofuran at a low temperature e.g. −78° C., yields a phenylselenyl intermediate of formulae 13(a) or 13(b):

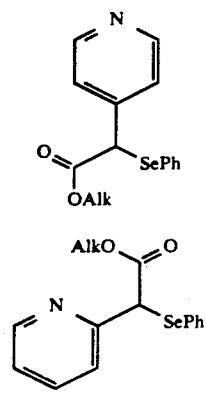

13(a)

13(b)

which may then be treated with a sodium periodiate/bicarbonate mixture in an aqueous alcohol at e.g. 0° C. to yield the intermediates of formulae 14(a) or 14(b):

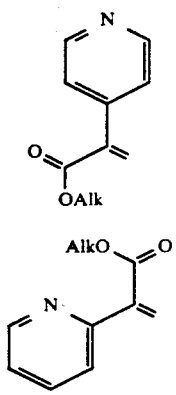

14(a)

14(b)

The group Alk may then be replaced in these intermediates with the desired group R, for example as described above with respect to the preparation of compounds of formula (1m).

According to a further aspect of the invention, we provide a cross-linking reagent of the invention, in particular a compound of formula (1), (2), (3) or (4), covalently linked to a chemical entity, leaving the thiol specific functional group available for reaction with a thiol group. Such a reagent may be kept ready for attachment to thiol groups of a desired polypeptide when required.

For example, the cross-linking reagent may be attached to a signal-producing chemical entity or a cytotoxic chemical entity leaving the free thiol reactive functional group. Such a compound can be stored and used for attachment to any suitable antibody, thus providing a flexible reagent for diagnostic and therapeutic applications. The compounds are more stable than those prepared using the known cross-linking reagents as a result of the greater specificity of the thiol-reactive functional group which reduces intermolecular reactions between molecules of the stored compound.

The invention is now described by way of example.

DESCRIPTION OF SPECIFIC EMBODIMENTS

In the following preparations of Intermediates and Examples, all melting points were recorded on an Electrothermal melting point apparatus and are uncorrected. When necessary solvents and reagents were dried before use. Pyridine and dimethylformamide were dried over 4A molecular sieves. Tetrahydrofuran was distilled from sodium ketal/benzophenone ketyl. Dichloromethane was distilled from calcium hydride. t-Butylchlorodiphenyl silane and 2-bromopyridine were dried over calcium hydride prior to use. Methyl triphenylphosphonium bromide was dried under vacuum. All non-aqueous reactions were carried out under a nitrogen atmosphere using oven dried glassware. Thin layer chromatography (T.l.c.) was performed on silica. All temperatures are in °C. "Dried" refers to drying over anhydrous magnesium sulphate.

Intermediate 1

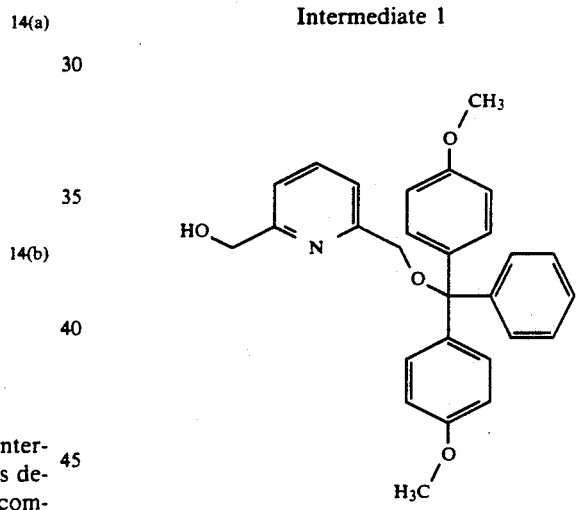

To a stirred solution of pyridine dimethanol (13.92 g) in dry pyridine (200 ml) was added dimethoxytrityl chloride (33.88 g) as a solution in pyridine (100 ml) dropwise over 3 h. The reaction mixture was stirred for a further 1 h and then concentrated by evaporation in vacuo. The reaction mixture was dissolved in CH$_2$Cl$_2$ (400 ml) and washed with saturated NaHCO$_3$ solution (400 ml). The aqueous fraction was further extracted with CH$_2$Cl$_2$ (400 ml) and the combined organic fractions dried, filtered and the solvent removed by evaporation in vacuo. Purification by flash chromatography, eluting with 8:2 diethyl ether/hexane gave Intermediate 1 (26.77 g) as a yellow glass, m.p. 38°–40°, T.l.c. Rf (8:2 diethyl ether/hexane) 0.20.

Intermediate 2

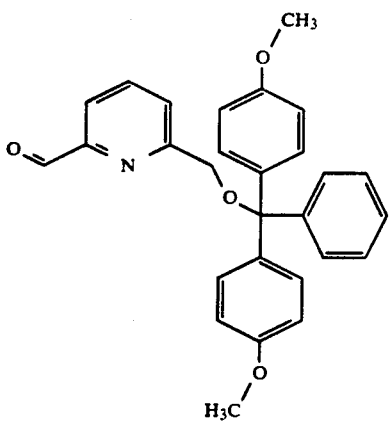

Intermediate 1 (22.08 g) was dissolved in dry CH₂Cl₂ (150 ml) and stirred at room temperature. Manganese dioxide (130.5 g) was added in a single portion and the reaction mixture stirred for 16 h and then filtered through celite to remove the excess manganese dioxide. The solvent was removed by evaporation in vacuo to give the crude product. Purification by flash chromatography, eluting with 1:1 diethyl ether/hexane gave Intermediate 2 (16.92 g) as a yellow glass, m.p. 43°–45°, T.l.c. Rf (1:1 diethyl ether/hexane) 0.35.

Intermediate 3

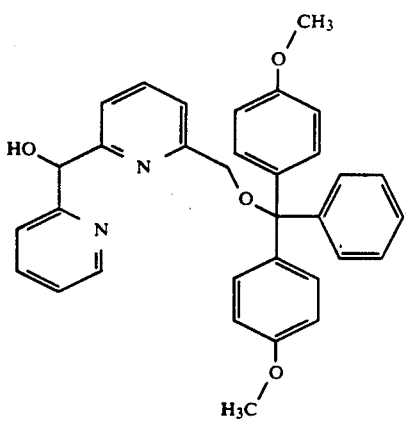

To a stirred solution of 2-bromopyridine (11.06 g) in dry tetrahydrofuran (150 ml) at −78° was added dropwise n-butyl lithium (43.75 ml of a 1.6M solution in hexane) ensuring that the temperature did not rise above −70°. The reaction was stirred for a further fifteen minutes. To the resulting deep red solution was added dropwise Intermediate 2 (29.75 g) as a solution in tetrahydrofuran (50 ml) dropwise. The violet solution formed was stirred for fifteen minutes at −78° and then allowed to warm to room temperature slowly. The reaction mixture was poured into saturated NaHCO₃ solution (200 ml) and extracted with CH₂Cl₂ (200 ml) twice. The combined organic fractions were dried, filtered and the solvent removed by evaporation in vacuo. Purification by flash chromatography, eluting with diethyl ether gave Intermediate 3 (31.22 g) as a yellow gum, T.l.c. Rf (diethyl ether) 0.22.

Intermediate 4

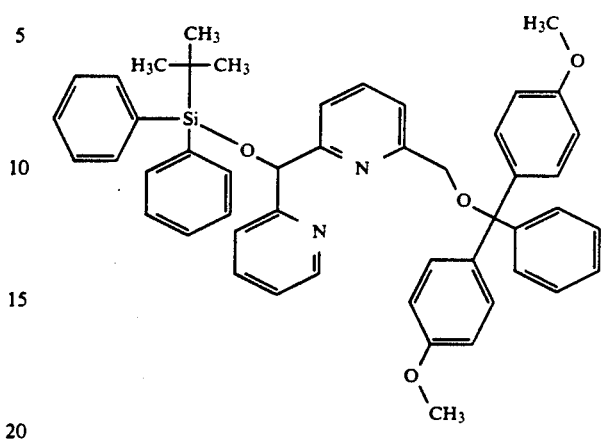

To a stirred solution of Intermediate 3 (16.54 g) in dry dimethylformamide (200 ml) was added imidazole (8.71 g) in a single portion followed by t-butylchlorodiphenyl silane (14.02 g), which was also added in a single portion. The reaction mixture was stirred for 72 h at room temperature and then the solvent was removed by evaporation in vacuo. The residue was dissolved in diethyl ether (200 ml) and washed with saturated NaHCO₃ solution (200 ml). The aqueous layer was further extracted with diethyl ether (200 ml), the combined organic fractions dried and solvent was removed by evaporation in vacuo. Purification by flash chromatography eluting with 1:1 diethyl ether/hexane gave Intermediate 4 (21.11 g) as a white glass, m.p. 50°–52°, T.l.c. Rf(1:1 diethyl ether/hexane) 0.22.

Intermediate 5

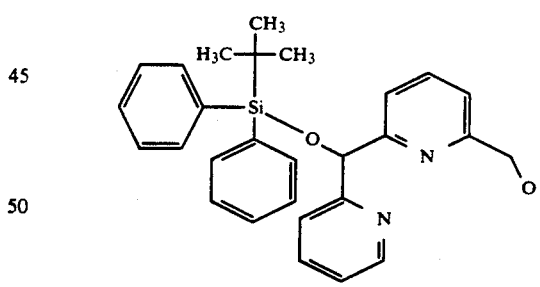

To a stirred solution of Intermediate 4 (10.0 g) in dry CH₂Cl₂ (200 ml) was added anhydrous zinc bromide (14.86 g) in a single portion. The reaction mixture was stirred for fifteen minutes and the resulting red solution poured into saturated NaHCO₃ solution (200 ml). The organic layer was separated and the aqueous layer further extracted with CH₂Cl₂ (200 ml). The combined organic fractions were dried, filtered and the solvent removed by evaporation in vacuo. Purification by flash chromatography eluting with diethyl ether gave Intermediate 5 (2.27 g) as a yellow oil, T.l.c. Rf (diethyl ether) 0.16.

Intermediate 6

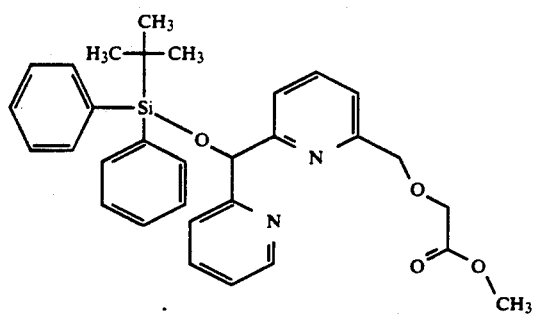

To a stirred solution of Intermediate 5 (2.27 g) in dry tetrahydrofuran (50 ml) at −78° was added dropwise n-butyl lithium (3.75 ml of a 1.6M solution in hexane). The reaction mixture was stirred for a further fifteen minutes at −78°. The resulting deep red solution was added via cannula to a solution of bromomethyl acetate (2.75 g) in tetrahydrofuran (25 ml) at 78°. The reaction mixture was stirred for 30 minutes at −78° and then allowed to warm to room temperature and stirred for a further 18 h. The reaction mixture was poured into saturated NaHCO$_3$ solution (150 ml) and extracted twice with CH$_2$Cl$_2$ (150 ml). The combined organic fractions were dried, filtered, and the solvent removed by evaporation in vacuo to give the crude product. Purification by flash chromatography eluting with diethyl ehter gave Intermediate 6 (1.92 g) as a yellow oil, T.l.c. Rf (diethyl ether) 0.30.

Intermediate 7

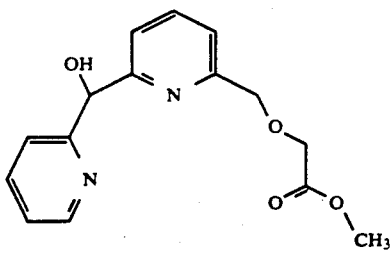

Intermediate 6 (1.92 g) was dissolved in dry tetrahydrofuran (20 ml) and to this solution was added tetrabutylammonium fluoride (3.65 ml of a 1M solution in tetrahydrofuran which contained five percent water). The reaction mixture was stirred for 16 h at room temperature and then poured into saturated NaHCO$_3$ solution (50 ml) and extracted twice with CH$_2$Cl$_2$ (50 ml). The combined organic fractions were dried, filtered and the solvent removed by evaporation in vacuo. Purification by flash chromatography, eluting with ethyl acetate gave Intermediate 7 (0.86 g) as a yellow oil, T.l.c. Rf (ethyl acetate) 0.23.

Intermediate 8

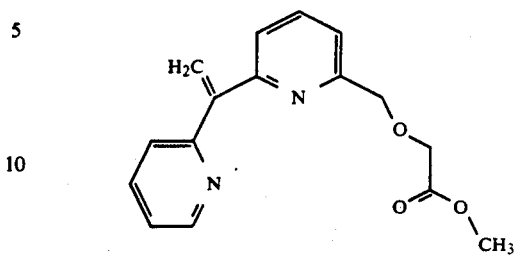

To a stirred solution of Intermediate 7 (0.86 g) in dry CH$_2$Cl$_2$ (50 ml) was added in a single portion manganese dioxide (7.83 g) and the reaction mixture stirred at room temperature for 16 h. The reaction was then filtered through celite to remove excess manganese dioxide and the solvent removed by evaporation in vacuo. Purification by flash chromatography eluting with CH$_2$Cl$_2$/i-propanol, gave Intermediate 8 (0.86 g) as an oil, T.l.c. Rf (19:1 CH$_2$Cl$_2$/i-propanol) 0.32.

EXAMPLE 1

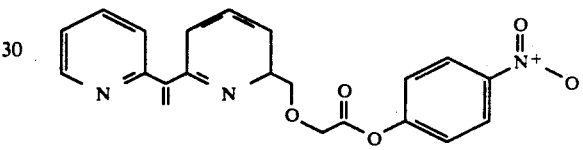

To a stirred suspension of methyl triphenylphosphonium bromide (0.337 g) in dry tetrahydrofuran (15 ml) at 0° was added n-butyl lithium (0.59 ml of a 1.6M solution in hexane) dropwise. The reaction mixture was allowed to warm to room temperature and stirred for a further hour. The resulting yellow solution was added dropwise at −78° via cannula to a solution of Intermediate 8 (0.27 g) in tetrahydrofuran (15 ml) (the solution of Intermediate 8 has prior to addition been stirred over 4 Å molecular sieves).

The reaction mixture was allowed to warm to room temperature and stirred for 3 h. The resulting white suspension was filtered through celite and the solvent removed by evaporation in vacuo. Purification by radial chromatography eluting with 19:1 CH$_2$Cl$_2$/1-butanol, gave the compound of Example 1 as a colourless oil, T.l.c. Rf (19:1 CH$_2$Cl$_2$/1-butanol) 0.13.

EXAMPLE 2

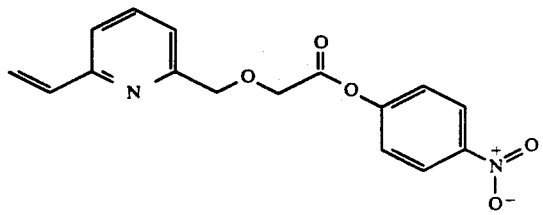

In this Example the various reactions and numbered compounds are those in Reaction Scheme A.

Reaction 1

Monoprotection of Pyridinedimethanol

To a stirred solution of pyridinedimethanol (7 g) in dry pyridine (100 ml) at room temperature under an inert atmosphere was added dimethoxytrityl chloride (16.94 g) as a solution in pyridine (50 ml) dropwise over 2 h. The reaction mixture was then stirred for a further 1 h, concentrated by evaporation in vacuo, and then dissolved in $CH_2Cl_2$ (200 ml), and washed with saturated $NaHCO_3$ solution (200 ml). The aqueous fraction was further extracted with $CH_2Cl_2$ (200 ml) and the combined organic fractions were dried, filtered and the solvent removed by evaporation in vacuo. Purification was by medium pressure column chromatography, eluting with 8:2 $Et_2O$/hexane, which gave 11.51 g of product I as a yellow solid.

Melting Point 38°–40°

NMR $\delta$ ($CDCl_3$) 7.30 (4H,d, 8.4 Hz, MeOCCHCCHCH) 6.73 (4H, d, 8.4 Hz, MeOCCHCHCCHCH), 6.60–7.73 (8H, m, aromatic), 4.55 (2H,s, $\overline{CH_2O}H$), 4.27 (2H, s, $CH_2OCAr_3$) and 3.63 (6H, s, OMe).

Reaction 2

Alkylation and Deprotection of Monoprotected Alcohol Product I

To a stirred suspension of NaH (0.84 g) in dry DMF (50 ml) under a nitrogen atmosphere at room temperature was added alcohol I (7.31 g) as a solution in DMF (50 ml) dropwise. Evolution of $H_2$ occurred and the reaction mixture was stirred for a further 1 h. The alkoxide so formed was added dropwise via cannula to a stirred solution of methylbromoacetate (3.98 g), in DMF (50 ml) at 0° C. and then stirred for a further 1 h. The reaction mixture was then poured into saturated $NaHCO_3$ solution (150 ml) and the product extracted twice with ether (200 ml). The combined organic fractions were dried ($MgSO_4$) and filtered.

The solvent was removed by evaporation in vacuo to give the crude product. Without purification the crude product was dissolved in 3:2 $CHCl_3$/methanol (250 ml) plus $H_2O$ (25 ml) and excess p-toluenesulphonic acid was added. The resulting deep red solution was stirred for a further 1 h and then poured into saturated $NaHCO_3$ solution (250 ml) and extracted twice with $CH_2Cl_2$ (250 ml). The combined organic fractions were dried filtered and the solvent removed by evaporation in vacuo. The crude product was purified by medium pressure column chromatography, eluting with 9:1 $CH_2Cl_2$/methanol which gave 1.78 g of alcohol II as a yellow oil.

Rf (9:1 $CH_2Cl_2$/methanol) 0.29

NMR $\delta$ ($CDCl_3$) 7.65 (q, 7.2 Hz, aromatic), 7.29 (t, 6.6 Hz, aromatic), 4.70 (4H, s, $CH_2O$), 4.19 (2H, s, $CH_2OC=O$), 4.20–4.45 (1H, brs, OH) and 3.73 (3H, s, OMe).

Mass Spec. $(M^+ + 1)$ 212.09228 ($C_{10}H_{14}NO_4$ requires 212.09228)

Reaction 3

Oxidation of Alcohol II to Aldehyde III

To a stirred solution of alcohol II (0.54 g) in dry $CH_2Cl_2$ (10 ml) was added, in a single portion, $MnO_2$ (6.53 g). The reaction mixture was stirred at room temperature and the reaction followed by tlc. When the tlc indicated that no alcohol was present, the reaction mixture was filtered (repeatedly if necessary) to remove excess $MnO_2$. The solvent was removed by evaporation in vacuo. Purification was by medium pressure column chromatography eluting with 8:2 ether/hexane. 0.34 g of aldehyde III, was isolated as an oil.

Rf (8:2 ether/hexane) 0.35

NMR $\delta$ ($CDCl_3$) 9.93 (1H, s, CH=O), 7.10–8.00 (3H, m, aromatic), 4.72 (2H, s, $CH_2O$), 4.18 (2H, s, $OCH_2$-C=O) and 3.63 (3H, s, OMe).

Mass Spec $(M^+ + 1)$ 210.0788 ($C_{10}H_{12}NO_4$ requires 210.7663)

Reaction 4

Wittig Reaction on Aldehyde III

To a stirred suspension of $Ph_3PMeBr$ (1.43 g; Ph=phenyl) in dry THF (10 ml) under a nitrogen atmosphere at room temperature was added n butyl lithium (2.58 ml of a 1.55M solution in hexane), dropwise to give a red solution. After stirring for a further 15 minutes the reaction mixture was stirred for 5 minutes at $-78°$ and then allowed to warm to room temperature, poured into $H_2O$ (20 ml) and extracted twice with ether (20 ml). The combined organic fractions were dried ($MgSO_4$) filtered and the solvent was removed by evaporation in vacuo. Purification was by radial chromatography, eluting with 1:1 ether/hexane, yielding 0.55 g of vinyl pyridine IV.

Rf (1:1) ether/hexane) 0.19

NMR $\delta$ ($CDCl_3$) 6.83–7.63 (3H, m, aromatic), 6.61 (1H, dd, 11, 17 Hz, CH=CH_2) 5.89, (1H, dd, 1.2, 7 Hz, $CH=CH_2$), 5.21 (1H, dd, 1.2, 11 Hz, $CH=CH_2$), 4.48 (2H, s, $\overline{CH_2}O$), 3.95 (2H, s, $OCH_2=O$) and 3.47 (3H, s, OMe).

Mass Spec. $(M^+ + 1)$ 208.0974 ($C_{11}H_{14}NO_3$ requires 208.0974)

Reaction 5

Deprotection and Esterification of Vinyl Pyridine IV

To a stirred solution of vinyl pyridine IV (0.06 g) in methanol (3 ml)-$H_2O$ (1 ml) plus $CH_2Cl_2$ to dissolve was added in one portion LiOH (0.012 g). The reaction mixture was stirred at room temperature and the reaction followed by tlc. When all the starting material had reacted the reaction mixture was concentrated by evaporation in vacuo, dissolved in pyridine and passed down a pyridinium Dowex column (20 fold excess). Removal of the solvent by evaporation in vacuo gave the deprotected acid as the pyridinium salt. The crude product was dissolved in dry $CH_2Cl_2$ (5 ml) and p-nitrophenol (0.063 g) added. To the stirred solution at room temperature was added dicyclohexylcyclodiimide (0.62 g) as a solution in $CH_2Cl_2$ (3 ml). After 10 minutes a precipitate formed. The reaction was stirred for a further 30 minutes. The reaction mixture was filtered, and the solvent removed by evaporation in vacuo. Purification was by radial chromatography, eluting with 2.5% ether/$CH_2Cl_2$, which gave the heterobifunctional cross-linking reagent of the invention, V in quantitative yield.

Rf (2.5% ether/$CH_2Cl_2$) 0.25

NMR $\delta$ ($CDCl_3$) 7.27–8.47 (7H, m. aromatic), 6.86 (1H, dd, 10, 4 Hz, $CH=CH_2$), 6.19 (1H, dd, 1, 14 Hz, $CH=CH_2$) 5.49 (1H, $\overline{dd}$, 1, 10 Hz, $CH=CH_2$), 4.85 (2H, s, $OCH_2$) and 4.51 (2H, s, $OCH_2C=O$).

Mass Spec. $(M^+ + 1)$ 315.09809 ($C_{16}H_{15}N_2O_5$ requires 315.09808)

Reaction Scheme A

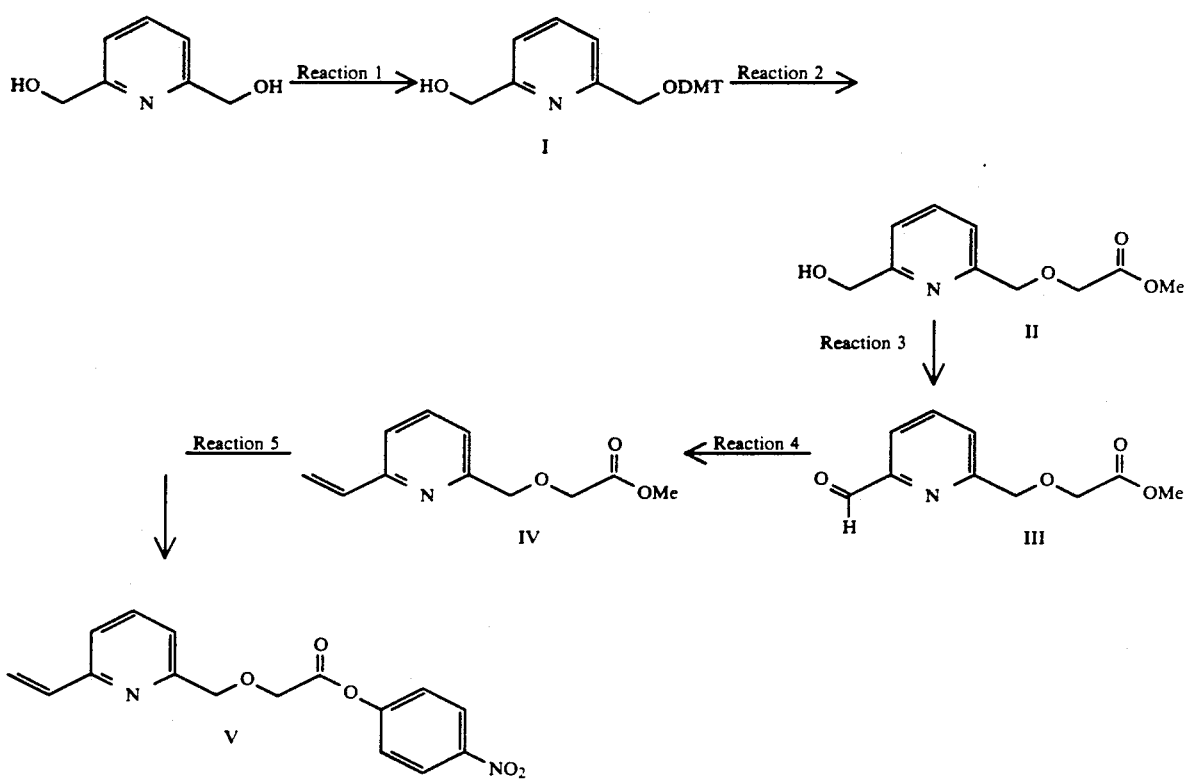

We claim:
1. A compound of the formula:

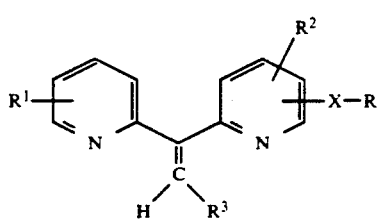

wherein X is a covalent bond or a, $C_{1-3}$ alkoxy $C_{1-3}$ alkylene, phenylene, or a $C_{5-7}$ cycloalkyl $C_{1-3}$ alkylene group; R is —$CO_2R^4$ where $R^4$ is an aryl or imide group and $R^1$, $R^2$, and $R^3$, which may be the same or different, is each a hydrogen atom or a halogen atom, —$NO_2$, —$CO_2H$, —$CO_2R^5$, —$COR^5$, —CHO, —CN —$CF_3$, —$SO_2NR^5R^6$ or a phenyl group where $R^5$ and $R^6$ are independently $C_{1-4}$ alkyl groups.

2. A compound of the formula:

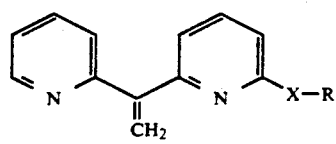

wherein X is a covalent bond or a, $C_{1-3}$ alkoxy $C_{1-3}$ alkylene, phenylene, or a $C_{5-7}$ cycloalkyl $C_{1-3}$ alkylene group, and R is —$CO_2R^4$ where $R^4$ is an aryl or imide group.

3. A compound of the formula (4):

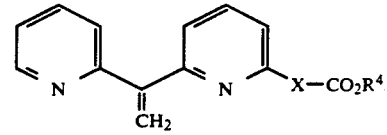

where X is a $C_{1-3}$alkoxy$C_{1-3}$alkylene, group and $R^4$ is a nitrophenyl or

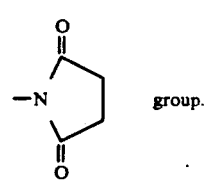

group.

4. A compound of formula:

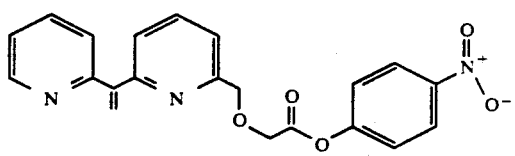

5. A compound of formula:

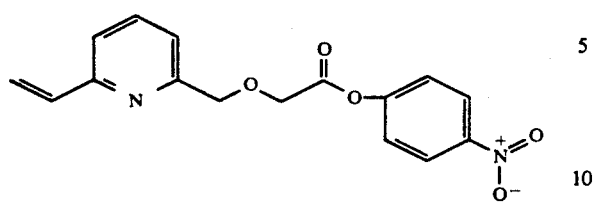
6. A compound of one of formulae (1a)–(1m):
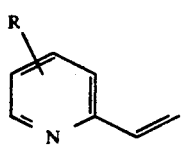
(1a)
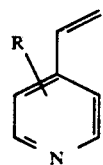
(1b)
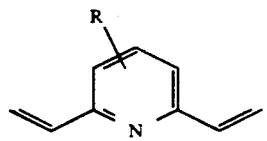
(1c)
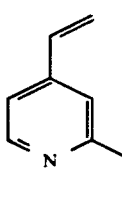
(1d)
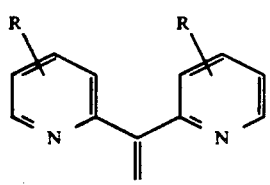
(1e)
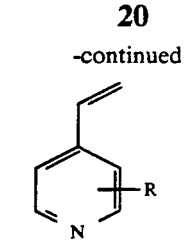
(1f)
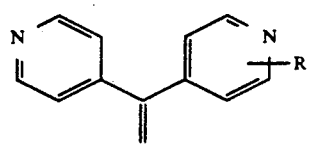
(1g)
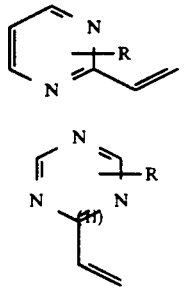
(1h)
(1i)
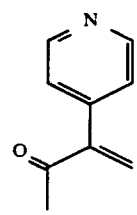
(1j)
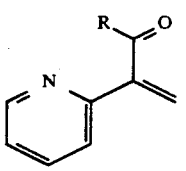
(1k)
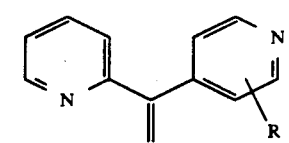
(1l)
(1m)
where R is $CO_2R^4$ where $R^4$ is an aryl or imide group.
* * * * *